(12) United States Patent
Shepard et al.

(10) Patent No.: US 10,627,364 B2
(45) Date of Patent: Apr. 21, 2020

(54) SYSTEMS AND METHODS FOR BIOLOGICAL ION CHANNEL INTERFACES

(71) Applicant: The Trustees of Columbia University in the City of New York, New York, NY (US)

(72) Inventors: Kenneth L. Shepard, Ossining, NY (US); Jacob Rosenstein, New York, NY (US); Siddharth Ramakrishnan, New York, NY (US); Jared Roseman, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 235 days.

(21) Appl. No.: 14/509,594

(22) Filed: Oct. 8, 2014

(65) Prior Publication Data

US 2015/0090588 A1    Apr. 2, 2015

Related U.S. Application Data

(63) Continuation of application No. PCT/US2013/031757, filed on Mar. 14, 2013.
(Continued)

(51) Int. Cl.
*G01N 27/414*    (2006.01)
*G01N 33/543*    (2006.01)
(Continued)

(52) U.S. Cl.
CPC ... *G01N 27/4148* (2013.01); *G01N 33/48728* (2013.01); *G01N 33/5438* (2013.01); *H05K 3/303* (2013.01); *Y10T 29/49147* (2015.01)

(58) Field of Classification Search
CPC ......... G01N 27/4148; G01N 33/48728; G01N 33/5438; H05K 3/303; Y10T 29/49147
See application file for complete search history.

(56) References Cited

U.S. PATENT DOCUMENTS

| 5,304,950 A | 4/1994 | Martin et al. |
|---|---|---|
| 5,599,668 A | 2/1997 | Stimpson et al. |

(Continued)

FOREIGN PATENT DOCUMENTS

| CN | 101126735 A | 2/2008 |
|---|---|---|
| CN | 101194162 A | 6/2008 |

(Continued)

OTHER PUBLICATIONS

J. Rosenstein, et al., Solid-State Nanopores Integrated with Low-Noise Preamplifiers for High-Bandwidth DNA Analysis, Life Science Systems and Applications Workshop (LiSSA), 2011 IEEE/NIH, pp. 59-62 (Apr. 7-8, 2011).*

(Continued)

*Primary Examiner* — Maris R Kessel
(74) *Attorney, Agent, or Firm* — Hunton Andrews Kurth LLP

(57) ABSTRACT

Method for interfacing an integrated circuit with a biological ion channel, the integrated circuit being at least partially disposed within an electrolytic solution and including an amplifier and one or more electrodes on a surface thereof, includes forming one or more microwells proximate the one or more electrodes, applying a lipid membrane over the integrated circuit proximate the microwells, and placing a further electrode in the electrolytic solution proximate the lipid membrane on a side opposite the integrated circuit. A biological ion channel interface is also provided.

20 Claims, 8 Drawing Sheets

Related U.S. Application Data

(60) Provisional application No. 61/622,234, filed on Apr. 10, 2012, provisional application No. 61/637,111, filed on Apr. 23, 2012.

(51) Int. Cl.
*G01N 33/487* (2006.01)
*H05K 3/30* (2006.01)

(56) References Cited

U.S. PATENT DOCUMENTS

| | | | |
|---|---|---|---|
| 6,030,115 | A | 2/2000 | Ishiguro et al. |
| 7,056,670 | B2 | 6/2006 | Odedra |
| 7,208,077 | B1 | 4/2007 | Albers et al. |
| 7,468,271 | B2 | 12/2008 | Golovchenko et al. |
| 7,491,628 | B2 | 2/2009 | Noca et al. |
| 7,635,423 | B2 | 12/2009 | Boussad et al. |
| 7,666,593 | B2 | 2/2010 | Lapidus |
| 7,767,400 | B2 | 8/2010 | Harris |
| 7,790,391 | B2 | 9/2010 | Harris et al. |
| 7,948,015 | B2 | 5/2011 | Rothberg et al. |
| 8,013,366 | B2 | 9/2011 | Lee et al. |
| 8,038,943 | B2 | 10/2011 | Yoo et al. |
| 9,625,404 | B2 | 4/2017 | Sorgenfrei et al. |
| 9,891,182 | B2 | 2/2018 | Sorgenfrei et al. |
| 2002/0006357 | A1 | 1/2002 | McGeoch et al. |
| 2002/0022226 | A1 | 2/2002 | Nakao et al. |
| 2003/0087292 | A1 | 5/2003 | Chen et al. |
| 2004/0028875 | A1 | 2/2004 | Van Rijn et al. |
| 2004/0055901 | A1 | 3/2004 | Petersen et al. |
| 2004/0238379 | A1 | 12/2004 | Lindsay et al. |
| 2005/0145496 | A1 | 7/2005 | Goodsaid et al. |
| 2005/0181383 | A1 | 8/2005 | Su et al. |
| 2005/0191495 | A1 | 9/2005 | Rueckes et al. |
| 2006/0078468 | A1 | 4/2006 | Gabriel et al. |
| 2006/0194263 | A1 | 8/2006 | Boussad et al. |
| 2006/0228402 | A1* | 10/2006 | Pohl ............. G01N 33/48728 424/450 |
| 2006/0240543 | A1 | 10/2006 | Folch et al. |
| 2006/0246443 | A1 | 11/2006 | Bockelmann et al. |
| 2006/0246497 | A1 | 11/2006 | Huang et al. |
| 2007/0275480 | A1* | 11/2007 | Brander ............. B82Y 5/00 436/501 |
| 2007/0292855 | A1 | 12/2007 | Dubin et al. |
| 2008/0035494 | A1 | 2/2008 | Gomez et al. |
| 2008/0094076 | A1 | 4/2008 | Hibbs et al. |
| 2008/0191718 | A1 | 8/2008 | Wolkow et al. |
| 2008/0203380 | A1 | 8/2008 | Wang et al. |
| 2008/0214494 | A1 | 9/2008 | Mohapatra et al. |
| 2008/0274912 | A1 | 11/2008 | Johnson et al. |
| 2009/0026082 | A1 | 1/2009 | Rothberg et al. |
| 2009/0142504 | A1 | 6/2009 | Ervin et al. |
| 2009/0173527 | A1 | 7/2009 | Benke et al. |
| 2009/0181381 | A1 | 7/2009 | Oldham et al. |
| 2009/0305319 | A1 | 12/2009 | Baudenbacher et al. |
| 2009/0325350 | A1 | 12/2009 | Radosavljevic et al. |
| 2010/0088040 | A1 | 4/2010 | Johnson, Jr. |
| 2010/0148126 | A1 | 6/2010 | Guan et al. |
| 2010/0285637 | A1 | 11/2010 | Khan et al. |
| 2010/0327874 | A1 | 12/2010 | Liu et al. |
| 2010/0331194 | A1* | 12/2010 | Turner ............. C12Q 1/6869 506/2 |
| 2011/0057725 | A1 | 3/2011 | Ikeda et al. |
| 2011/0101996 | A1 | 5/2011 | Potyrailo et al. |
| 2011/0105870 | A1 | 5/2011 | Dale et al. |
| 2011/0117582 | A1 | 5/2011 | Malima et al. |
| 2011/0147714 | A1 | 6/2011 | Hong et al. |
| 2011/0165572 | A1 | 7/2011 | O'Halloran |
| 2011/0220775 | A1 | 9/2011 | Triener et al. |
| 2011/0263463 | A1 | 10/2011 | Rothberg et al. |
| 2011/0311427 | A1 | 12/2011 | Hauge et al. |
| 2012/0019270 | A1* | 1/2012 | Amodei ........... G01N 33/48728 324/692 |
| 2012/0025414 | A1 | 2/2012 | Schmidt et al. |
| 2012/0061239 | A1 | 3/2012 | Elibol et al. |
| 2012/0064519 | A1 | 3/2012 | Fang et al. |
| 2012/0234679 | A1 | 9/2012 | Garaj et al. |
| 2013/0078622 | A1 | 3/2013 | Collins et al. |
| 2013/0180867 | A1 | 7/2013 | Rosenstein et al. |
| 2013/0285680 | A1 | 10/2013 | Sorgenfrei et al. |
| 2018/0059040 | A1 | 3/2018 | Sorgenfrei et al. |

FOREIGN PATENT DOCUMENTS

| | | |
|---|---|---|
| CN | 101346472 A | 1/2009 |
| WO | WO 2006/024023 | 3/2006 |
| WO | WO 2007/075967 A2 | 7/2007 |
| WO | WO 2008/132643 | 11/2008 |
| WO | WO 2009/046110 | 4/2009 |
| WO | WO 2010/030057 | 3/2010 |
| WO | WO 2011/123525 | 10/2011 |
| WO | WO 2012/021149 | 2/2012 |
| WO | WO 2012/042226 | 4/2012 |
| WO | WO 2012/044857 | 4/2012 |

OTHER PUBLICATIONS

U.S. Appl. No. 13/787,341 (US 2013/0180867), filed Mar. 6, 2013 (Jul. 18, 2013).

U.S. Appl. No. 13/942,242 (US 2014/0048416), filed Jul. 15, 2013 (Feb. 20, 2014).

U.S. Appl. No. 13/801,834 (US 2013/0285680), filed Mar. 13, 2013 (Oct. 31, 2013).

U.S. Appl. No. 13/595,106 (US 2013/0224879), filed Aug. 27, 2012 (Aug. 29, 2013).

U.S. Appl. No. 14/509,766 (US 2015/0093849), filed Oct. 8, 2014 (Apr. 2, 2015).

U.S. Appl. No. 13/787,341, dated Jun. 12, 2015 Notice of Allowance.

U.S. Appl. No. 13/787,341, dated Apr. 14, 2015 Response to Non-Final Office Action.

U.S. Appl. No. 13/787,341, dated Jan. 15, 2015 Non-Final Office Action.

U.S. Appl. No. 13/942,242, dated Jan. 22, 2015 Non-Final Office Action.

U.S. Appl. No. 13/595,106, dated Jun. 24, 2015 Notice of Allowance.

U.S. Appl. No. 13/595,106, dated Dec. 18, 2014 Amendment and Request for Continued Examination (RCE).

U.S. Appl. No. 13/595,106, dated Dec. 18, 2014 Response after Final Office Action.

U.S. Appl. No. 13/595,106, dated Oct. 6, 2014 Applicant Initiated Interview Summary.

U.S. Appl. No. 13/595,106, dated Jun. 25, 2014 Final Office Action.

U.S. Appl. No. 13/595,106, dated May 5, 2014 Response to Non-Final Office Action.

U.S. Appl. No. 13/595,106, dated Apr. 25, 2014 Applicant Initiated Interview Summary.

U.S. Appl. No. 13/595,106, dated Feb. 5, 2014 Non-Final Office Action.

Anderson, et al., "A Label-free CMOS DNA Microarray based on Charge Sensing", Instrumentation and Measurement Technology Conference Proceedings, May 12-15, 2008, pp. 1631-1636.

Arata, et al., "Millisecond Analysis of Double Stranded DNA with Flourescent Intercalator by Micro-Thermocontrol-Device", *Talanta*, 79(3):963-966 (2009).

Barilero, et al., "Fluorescent thermometers for dual-emission wavelength measurements: Molecular engineering and application to thermal imaging in a microsystem" *Analytical Chemistry*, 2009, 81(19): 7988-8000.

Barilero, et al., *Analytical Chemistry*, 2009, 81: supplemental information.

Besteman, K. et al., "Enzyme-coated carbon nanotubes as single molecule biosensors", *Nano Letters, American Chemical Society*, vol. 3, No. 6, Jan. 5, 2003, pp. 727-730, XP002982648.

CN Office Action dated Nov. 19, 2014 in CN Patent Application No. 201280004265.8.

(56) References Cited

OTHER PUBLICATIONS

Extended EP Search Report dated Dec. 15, 2014 in EP Application No. 12734088.
Fu et al., "Label-free electrical detection of DNA hybridization using carbon nanotubes and graphene", *Nano Reviews*, vol. 1, No. 0, Aug. 31, 2010, XP055158479.
Goldsmith, et al., "Monitoring Single-Molecule Reactivity on a Carbon Nanotube", *Nano Letters*, 2008. 8(1): p. 189-194.
Goldsmith, et al., "Conductance-Controlled Point Functionalization of Single-Walled Carbon Nanotubes", *Science*, 2007. 315(5808): p. 77-81.
Gudnason, et al., "Comparison of Multiple DNA Dyes for Real-Time PCR: Effects of Dye Concentration and Sequence Composition on DNA Amplification and Melting Temperature", *Nucleic Acids Reasearch*, 35(19):e127 (2007).
Hazani et al., "Confocal Fluorescence Imaging of DNA-Functionalized Carbon Nanotubes", *Nano Letters*, vol. 3, No. 2, Feb. 1, 2003, pp. 153-155, XP055157827.
Heller, et al., "Identifying the mechanism of biosensing with carbon nanotube transistors", *Nano Letters*, 2008. 8(2): p. 591-5.
Huang, et al., "Gene expression analysis with an integrated Cmos microarray by time-resolved fluorescence detection", *Biosensors and Bioelectronics*, vol. 26, pp. 2660-2665.
Kang, et al., "High-performance electronics using dense, perfectly aligned arrays of single-walled carbon nanotubes", *Nat Nano*, 2007. 2(4): p. 230-236.
Kim, et al., "Nanopore sensor for fast label-free detection of short double-stranded DNAs", *Biosensors and Bioelectronics*, vol. 22, Issue 12, pp. 2926-2931.
Levine, et al., "Real-time, multiplexed electrochemical DNA detection using an active complementary metal-oxide-semiconductor biosensor array with integrated sensor electronics", *Biosensors and Bioelectronics*, vol. 24, No. 7, pp. 1995-2001.
Meric, et al., "Hybrid carbon nanotube-silicon complementary metal oxide semiconductor circuits", *Journal of Vacuum Science & Technology B*, 2007. 25(6): p. 2577-2580.
Mortazavi, et al., "Mapping and quantifying mammalian transcriptomes by RNA-Seq.", *Nature Methods*, 2008. 5(7): p. 621-628.
Polk, et al., "Ag/AgCl microelectrodes with improved stability for microfluidics", *Sensors & Actuators: B. Chemical*, 2006. 114: p. 239-247.
Rosenblatt, et al., High performance electrolyte gated carbon nanotube transistors. Nano Letters, 2002. 2(8): p. 869-872.
Rosenstein, et al., "Integrated nanopore sensing platform with sub-microsecond temporal resolution", Nature Methods, Mar. 3, 2012.
So, et al., "Single-Walled Carbon Nanotube Biosensors Using Aptamers as Molecular Recognition Elements", *Journal of the American Chemical Society*, vol. 127, No. 34, Aug. 1, 2005, pp. 11906-11907, XP55032046.
Sorgenfrei et al., "Label-free single-molecule detection of Dna-hybridization kinetics with a carbon nanotube field-effect transistor", *Nature Nanotechnology*, vol. 6, No. 2, Jan. 23, 2011, pp. 126-132, XP055157740.
Sorgenfrei, et al., "Single-molecule electronic detection using nanoscale field-effect devices", Design Automation Conference (DAC), Jun. 5-9, 2011.
Sorgenfrei, et al., "Debye Screening in Single-Molecule Carbon Nanotube Field-Effect Sensors", *Nano Letters*, 2011. 11(9): p. 3739-3743.
Star, et al., "Label-free detection of DNA hybridization using carbon nanotube network field-effect transistors", Proceedings of the National Academy of Sciences, vol. 103, No. 4, Jan. 24, 2006, pp. 921-926, XP003023787.
Suzuki, et al., "Microtechnologies for membrane protein studies", *Anal Bioanal Chem.*, 391(8):2695-2702 (2008).
Tashiro, et al., "A Nanothermometer Based on the Different pi Stacking of B- and Z-DNA", *Angewandte Chemie International Edition*, 42(18):6018-6020 (2003).
Tashiro, et al., "The Molecular-Thermometer Based on B-Z- Transition of DNA", Nucleic Acids Symposium Series, 48(1):89-90 (2004).
Wanunu, et al., "Electrostatic focusing of unlabelled DNA into nanoscale pores using a salt gradient", *Nat Nano*, 2010. 5(2): p. 160-165.
Yin, et al. (IEEE, 2007).
Zhao, et al., "Stochastic sensing of biomolecules in a nanopore sensor array", *Nanotechnology*, vol. 19, No. 50, pp. 505504.
International Search Report and Written Opinion for PCT/US2013/031757, dated Jun. 4, 2013.
International Search Report and Written Opinion for PCT/US2013/031745, dated Jun. 4, 2013.
International Search Report and Written Opinion for PCT/US2012/026292, dated May 29, 2012.
International Search Report and Written opinion for PCT/US2012/020955, dated May 16, 2012.
U.S. Appl. No. 14/837,514 (US 2015/0369776), filed Aug. 27, 2015 (Dec. 24, 2015).
U.S. Appl. No. 13/787,341, dated Nov. 16, 2015 Issue Fee Payment.
U.S. Appl. No. 13/787,341, dated Aug. 20, 2015 Notice of Allowance.
U.S. Appl. No. 13/787,341, dated Aug. 12, 2015 Request for Continued Examination (RCE).
U.S. Appl. No. 13/801,834, dated Apr. 20, 2016 Non-Final Office Action.
U.S. Appl. No. 13/801,834, dated Jan. 27, 2016 Response to Non-Final Office Action.
U.S. Appl. No. 13/801,834, dated Jul. 28, 2015 Non-Final Office Action.
U.S. Appl. No. 13/942,242, dated Jul. 30, 2015 Notice of Abandonment.
U.S. Appl. No. 13/595,106, dated Sep. 24, 2015 Issue Fee Payment.
U.S. Appl. No. 13/595,106, dated Dec. 9, 2013 Response to Restriction Requirement.
U.S. Appl. No. 13/595,106, dated Jul. 25, 2013 Restriction Requirement Filed.
U.S. Appl. No. 14/509,766, dated Apr. 20, 2016 Non-Final Office Action.
Feldman et al., "Molecular Electronic Devices Based on Single-Walled Carbon Nanotube Electrodes," Accounts of Chemical Chemical Research 41(12):1731-1741 (Dec. 2008).
Guo et al., "Functional single-molecule devices based on SWNTs as point contacts," Journal of Materials Chemistry 19:5470-5473 (2009).
Liu et al., "Translocation of Single-Stranded DNA Through Single-Walled Carbon Nanotubes," Science 327(5961):64-67 (2010).
Yin et al., "A Low-Noise Preamplifier with Adjustable Gain and Bandwidth for Biopotential Recording Applications", IEEE, 2007, pp. 321-324.
U.S. Appl. No. 15/453,628 (US 2018/0059040), filed Mar. 8, 2017 (Mar. 1, 2018).
U.S. Appl. No. 15/646,880 (U.S. Pat. No. 9,891,182), filed Jul. 11, 2017 (Feb. 13, 2018).
U.S. Appl. No. 15/799,044 (US 2018/0045717), filed Oct. 31, 2017 (Feb. 15, 2018).
U.S. Appl. No. 15/857,010 (U.S. 2018/0156746), filed Dec. 28, 2017 (Jun. 7, 2018).
15/453,628, dated Aug. 9, 2018 Non-Final Office Action.
U.S. Appl. No. 15/646,880, dated Dec. 28, 2017 Issue Fee Payment.
U.S. Appl. No. 15/646,880, dated Dec. 4, 2017 Notice of Allowance.
U.S. Appl. No. 15/646,880, dated Oct. 23, 2017 Applicant Initiated Interview Summary.
U.S. Appl. No. 15/799,044, dated Jul. 27, 2018 Non-Final Office Action.
U.S. Appl. No. 15/857,010, dated Aug. 13, 2018 Non-Final Office Action.
U.S. Appl. No. 15/857,010, dated Jun. 19, 2018 Response to Non-Final Office Action.
U.S. Appl. No. 15/857,010, dated Apr. 6, 2018 Non-Final Office Action.

(56) References Cited

OTHER PUBLICATIONS

Veetil et al., "Development of Immunosensors Using Carbon Nanotubes," Biotechnology Progress, 23:517-531 (2007).

* cited by examiner

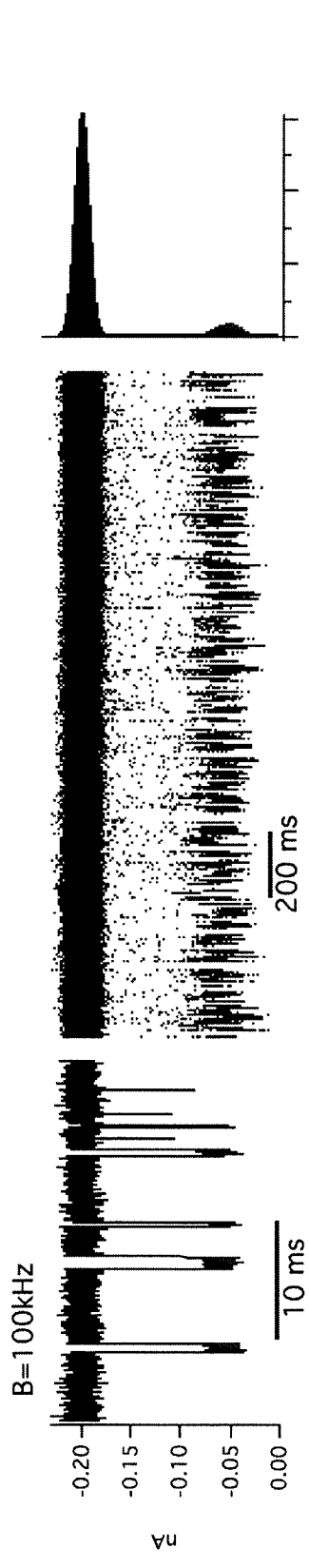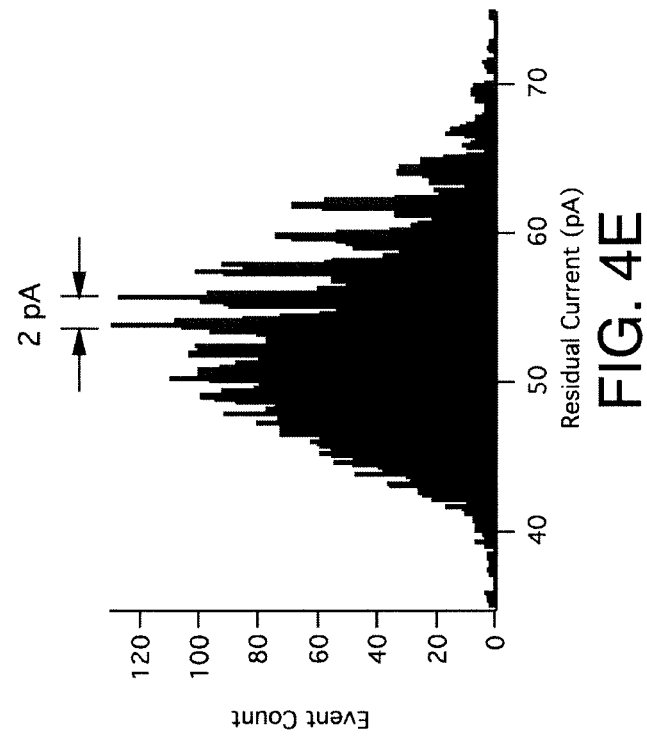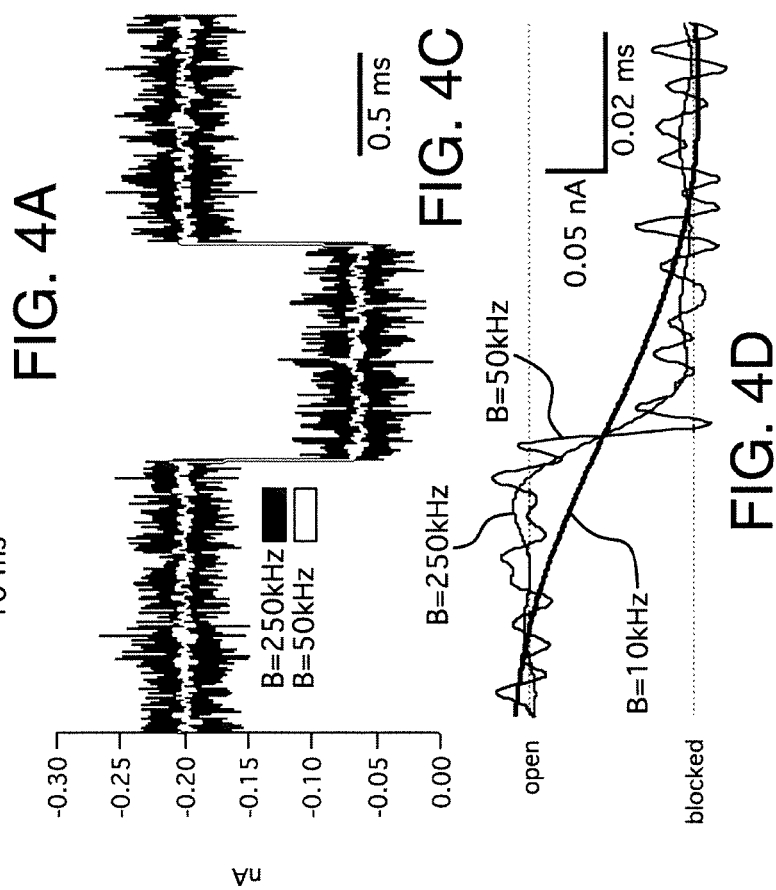

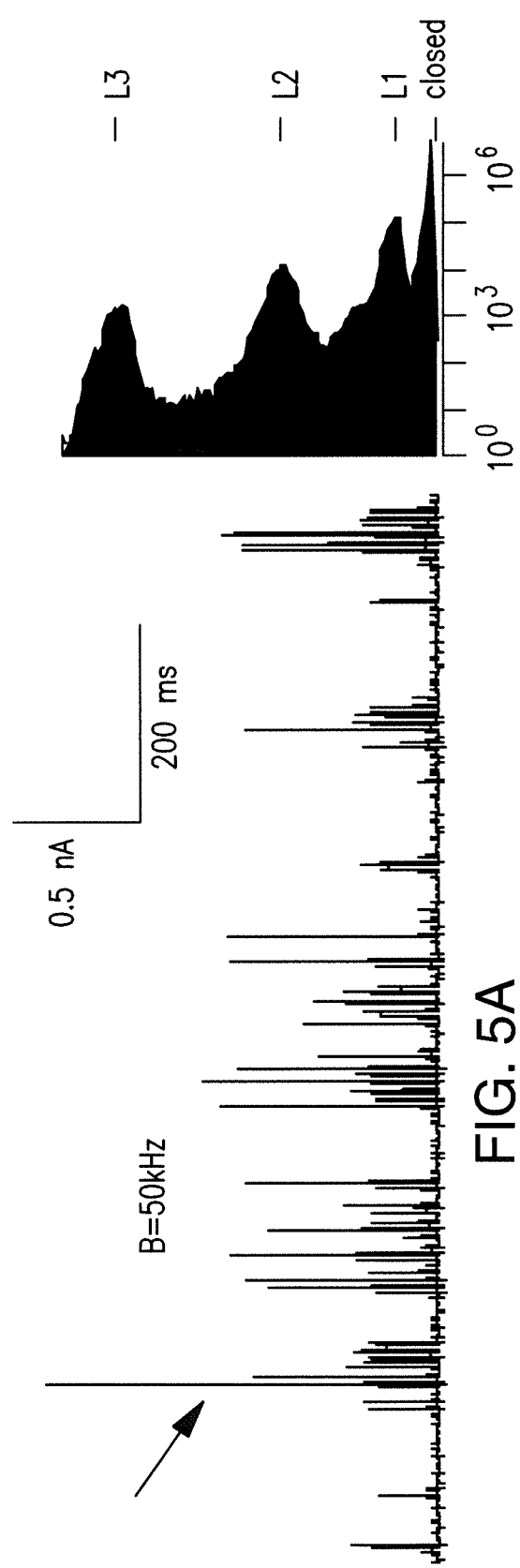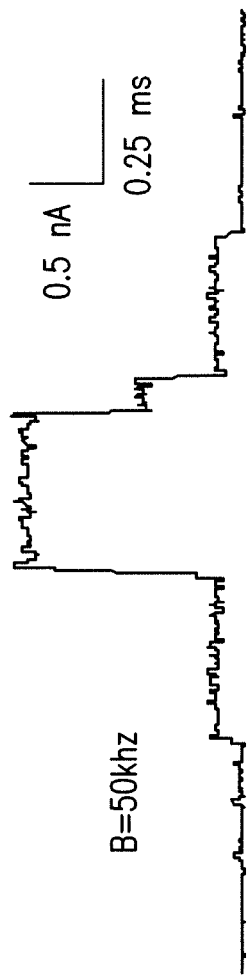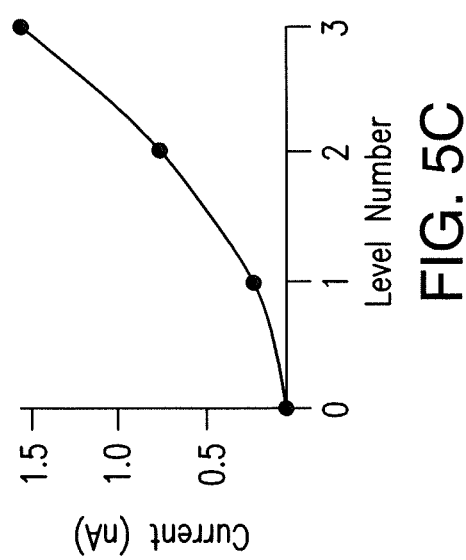
FIG. 5A
FIG. 5B
FIG. 5C
FIG. 5D

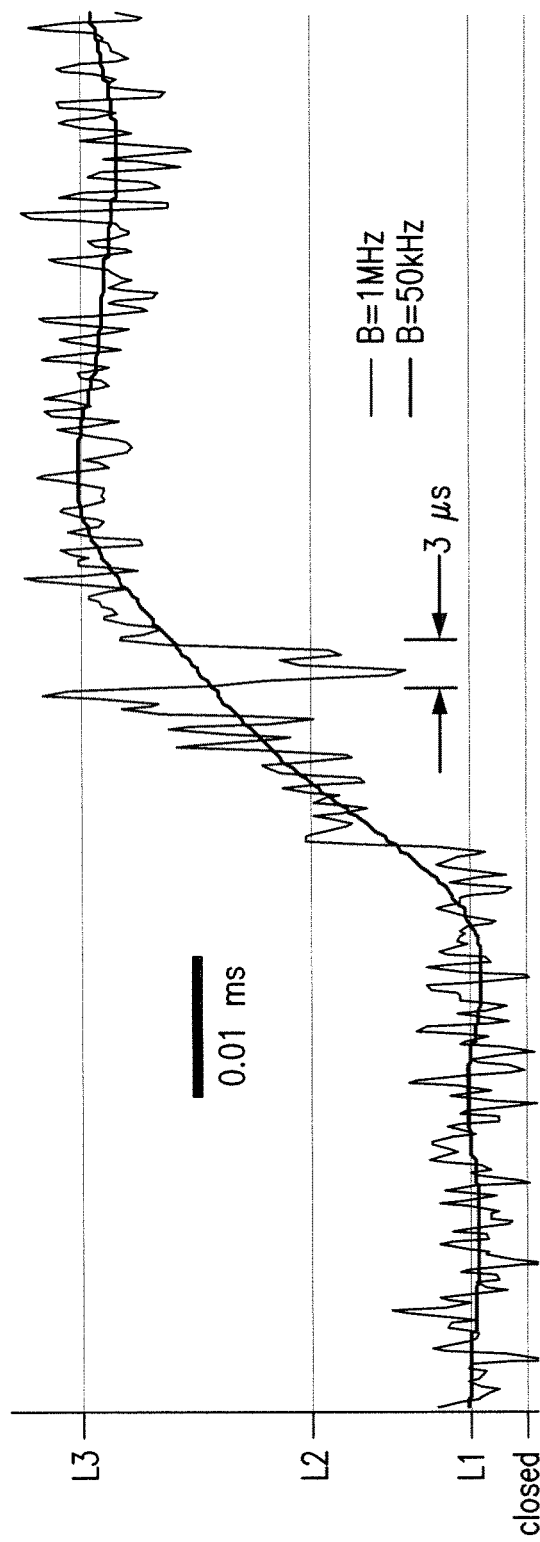
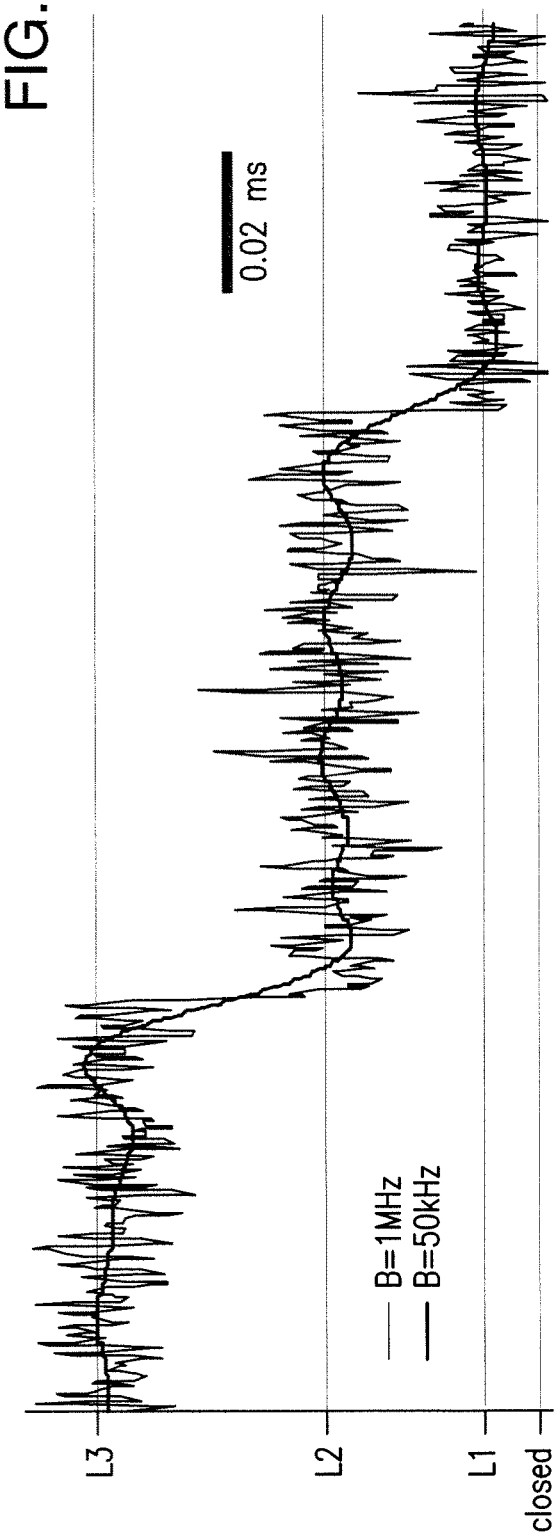
FIG. 6A
FIG. 6B

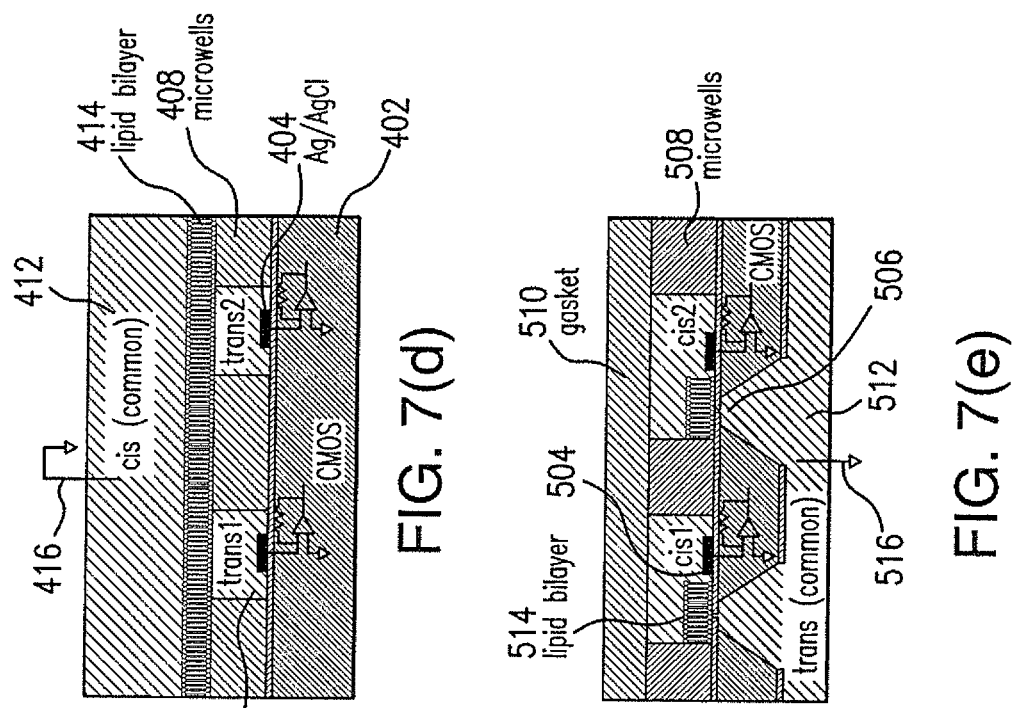
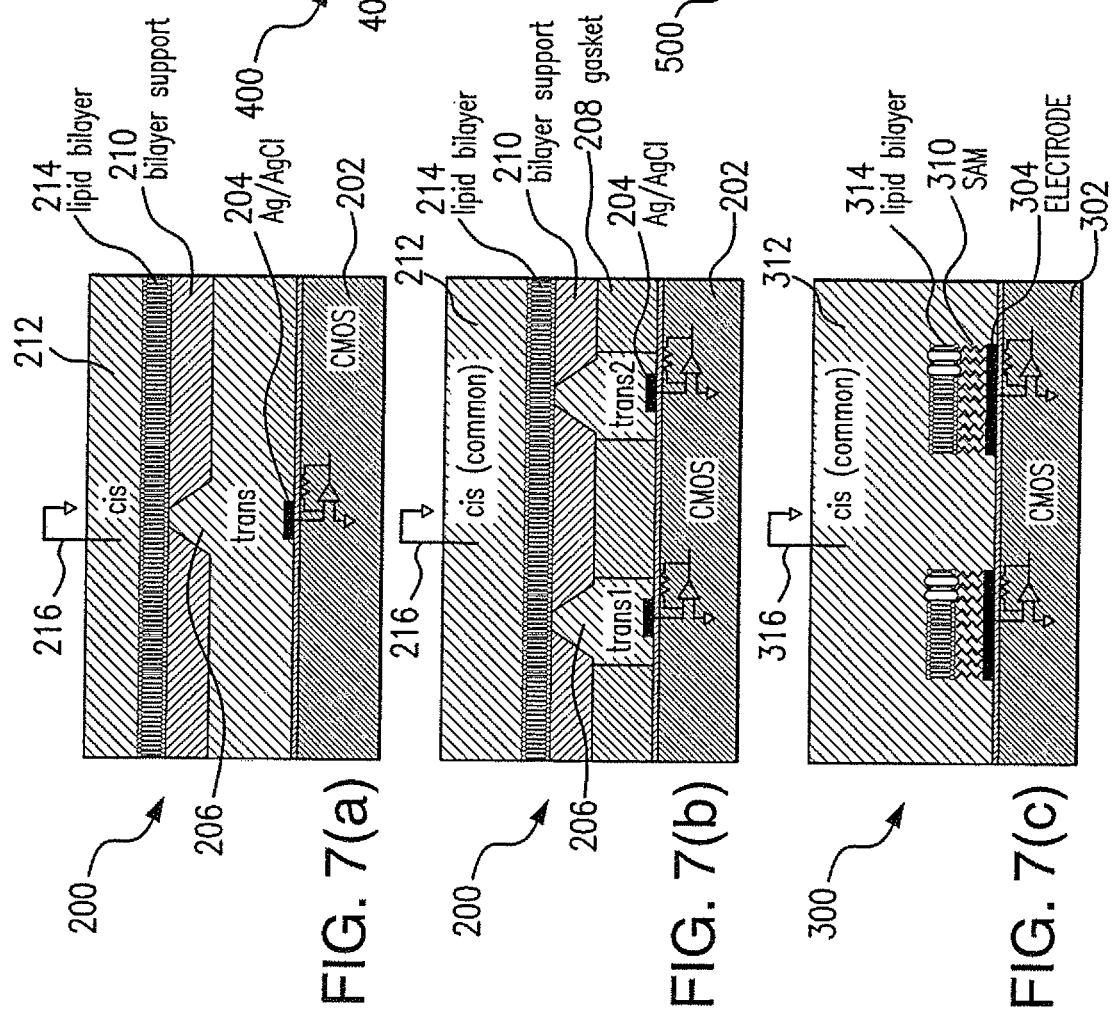

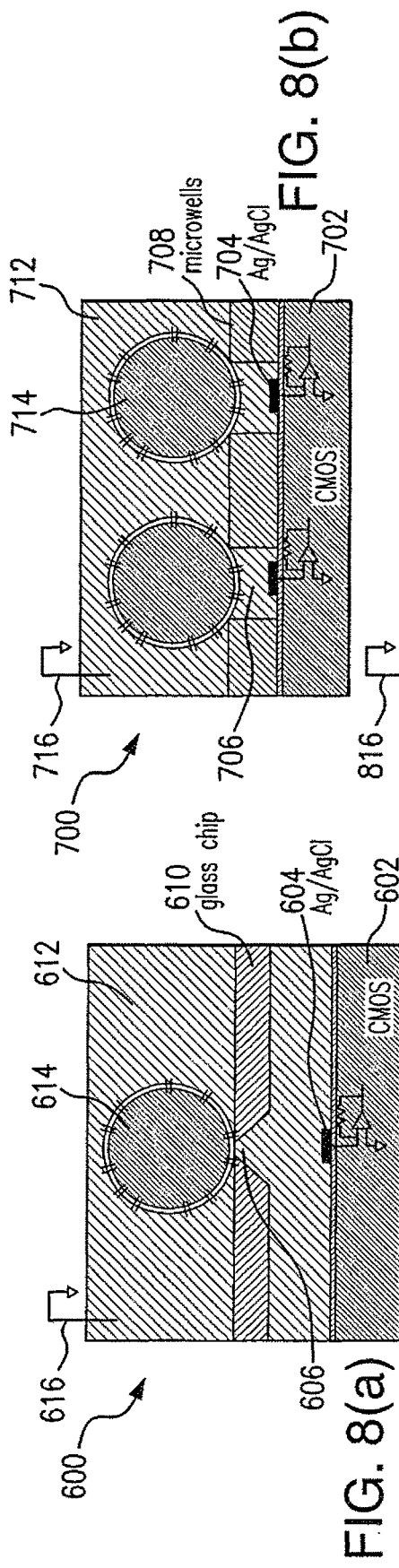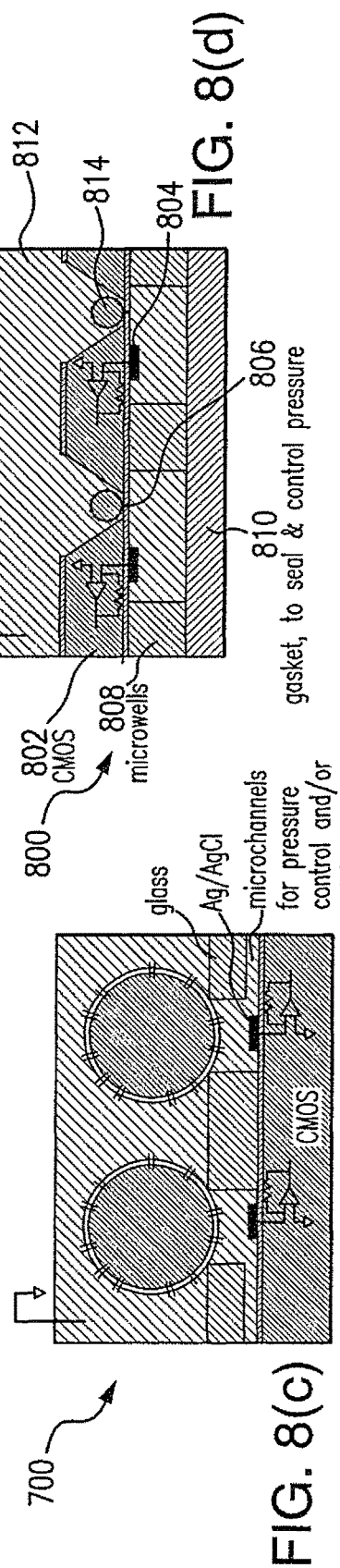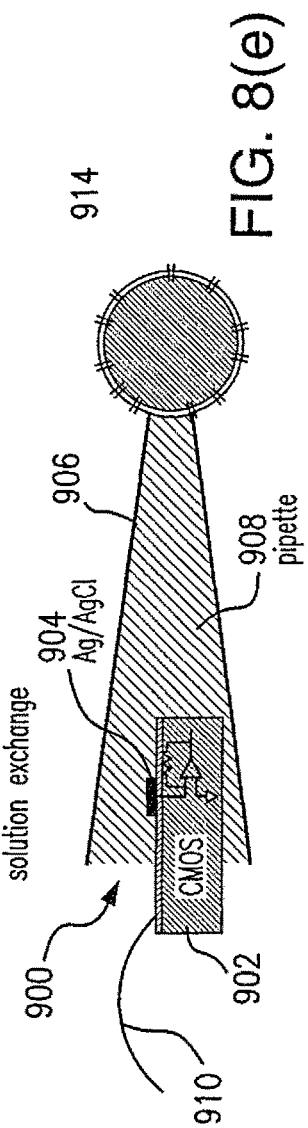

US 10,627,364 B2

SYSTEMS AND METHODS FOR BIOLOGICAL ION CHANNEL INTERFACES

CROSS-REFERENCE TO RELATED APPLICATIONS

This application claims priority to U.S. Provisional Patent Application Ser. No. 61/622,234, filed on Apr. 10, 2012, Ser. No. 61/637,111, filed on Apr. 23, 2012, each which is incorporated by reference herein in their entireties.

STATEMENT REGARDING FEDERALLY-SPONSORED RESEARCH

This invention was made with government support under HG003089 and HG006879 awarded by the National Institutes of Health. The government has certain rights in the invention.

BACKGROUND

The disclosed subject matter relates to biological ion channel interfaces, including techniques for interfacing biological ion channels with integrated CMOS amplifiers.

Ion channel proteins can generally be found in the cellular membranes of living things. Certain functions of ion channels, including sensing, signaling and energetics, can have important applications, for example and without limitation, to drug discovery. Yet, certain characteristics of ion channels, including the stochastic behavior and delicate structure of ion channels, can present challenges, for example in understanding some of the biomolecular mechanisms and dynamics of channel gating, as well as in reliably utilizing isolated ion channels for biotechnology platforms, including nanopore DNA sequencing.

Ion channels can be analyzed using patch-clamp techniques. Furthermore, biophysical studies of some ion channels can utilize in vitro planar reconstituted lipid bilayers as model cell membranes. Reconstituted bilayers can be suitable at least because they have a chemical makeup that can be well-controlled, generally involve no live cells and can be measured outside physiological conditions, and have a planar geometry suitable for electrochemical measurements.

Electronic measurements of ion channels in both patch-clamp and planar bilayer experiments can be made with voltage-clamp amplifiers, which can measure the ionic current through a lipid membrane while applying an electrochemical potential through electrodes. Single-channel conductance can vary between types of ion channels, but generally have nanoscale dimensions producing currents on the order of picoamperes or less. These relatively weak signals can approach the noise floor of typical electronic amplifiers, and single-channel recordings can generally be constrained in both amplitude and temporal resolution by low signal-to-noise ratios.

Lipid bilayer recordings can have high-frequency noise, which can be a function of experimental capacitances. The equivalent input voltage noise of a voltage-clamp amplifier $v_n$ (V $Hz^{-1/2}$) can produce noise currents through input capacitances ($\Sigma C$), with a root-mean squared amplitude that can be represented as:

$$I_{RMS} = \frac{2\pi}{\sqrt{3}} B^{\frac{3}{2}} v_n \sum C \quad (1)$$

where B can represent the measurement bandwidth. One capacitance in lipid bilayer experiments can be that of the lipid membrane itself ($C_M$), and lipid bilayers, which can be a few nanometers thick, can have specific capacitance on the order of 0.5 µF/cm². Circular planar bilayers diameters ranging from 1 µm-200 µm can thus have $C_M$ ranging from 4 fF to 80 pF.

However, there remains an opportunity for improved biological ion channels with reduced parasitic capacitance in biological ion channel recordings and can provide multiple independent recordings on a single chip with improved signal bandwidths.

SUMMARY

Systems and methods for biological ion channel interfaces, including interfacing an integrated circuit with a biological ion channel, are disclosed herein.

According to one aspect of the disclosed subject matter, methods for interfacing an integrated circuit with a biological ion channel are provided. In one example where the integrated circuit is at least partially disposed within an electrolytic solution and includes an amplifier and one or more electrodes on a surface thereof, the method can include forming one or more microwells proximate the one or more electrodes, applying a lipid membrane over the integrated circuit proximate the microwells, and placing a further electrode in the electrolytic solution proximate the lipid membrane on a side opposite the integrated circuit.

In some embodiments, the lipid membrane can include a reconstituted lipid bilayer. The lipid bilayer can include one or more reconstituted lipids in oil. The one or more reconstituted lipids can include diphytanoyl phosphatidylcholine. The oil can include n-octane, n-decane or n-hexadecane. Additionally or alternatively, the lipid membrane can include a cellular membrane of a live cell. Applying the lipid membrane can include applying a pressure differential between the live cell and the one or more microwells. As such, the method can further include forming microchannels along the integrated circuit proximate microwells to control the pressure differential proximate the microwells.

In another example, an intermediate structure, which has one or more microwells and is adapted to be disposed in the electrolytic solution proximate the one or more electrodes, is provided. A lipid membrane can be disposed proximate the one or more, and a further electrode can be provided to be disposed in the electrolytic solution proximate the lipid bilayer on a side opposite the integrated circuit.

In some embodiments, the lipid membrane can include a reconstituted lipid bilayer. The lipid bilayer can include one or more reconstituted lipids in oil. The one or more reconstituted lipids can include diphytanoyl phosphatidylcholine. The oil can include n-octane, n-decane or n-hexadecane. Additionally or alternatively, the lipids can include one or more unilamellar lipid vesicles. Additionally or alternatively, the lipid membrane can include a cellular membrane of a live cell. One or more microchannel can be provided along the integrated circuit proximate the one or more microwells to control a pressure differential between the one or more microwells and the live cell. The one or more electrodes can include an Ag/AgCl electrode.

According to another aspect of the disclosed subject matter, methods for interfacing an integrated circuit with a biological ion channel are provided. An example method can include inserting at least a first end of an integrated circuit including the one or more electrodes into a first end of a pipette containing an electrolytic solution, coupling a cell to a second end of the pipette, and placing an electrical lead wire on a second end of the integrated circuit.

BRIEF DESCRIPTION OF THE DRAWINGS

FIGS. 4A-4E are diagrams illustrating further features of the exemplary biological ion channel interface of FIG. 1A.

FIG. 5A-5D are diagrams illustrating further features of the exemplary biological ion channel interface of FIG. 1A.

FIGS. 6A-6B are diagrams illustrating further features of the exemplary biological ion channel interface of FIG. 1A.

FIGS. 7A-7E each illustrates another exemplary embodiment of a biological ion channel interface according to the disclosed subject matter.

FIGS. 8A-8E each illustrates another exemplary embodiment of a biological ion channel interface according to the disclosed subject matter.

DETAILED DESCRIPTION

The disclosed subject matter provides systems and methods for a biological ion channel interface. Biological ion channel interfaces can be utilized to perform single-ion-channel recordings, for example and without limitation, of lipid membranes and/or whole cells. Biological ion channel interfaces according to the disclosed subject matter can be used, for example and without limitation, in ion channel studies to study the electrochemical behavior of membrane ion channels The interfaces can further be used in biological nanopore platforms, for example as "nanopore" sensors, with which other molecules can be detected when occupying a channel and modulating its ionic conductance. Such sensors can be used, for example and without limitation, in DNA sequencing. Furthermore, the interfaces can be used, for example and without limitation, for drug discovery, evaluation and safety screening, in which tightly-integrated ion channel interface electronics can improve the throughput of ion channel drug screening platforms.

Another exemplary application of the interfaces is for use with implantable sensors. For example, covering an integrated circuit with reconstituted lipids improve biocompatibility of the circuit, for example for implantable applications or long-duration experiments. Furthermore, the interfaces can be used in chemical or environmental sensors. In this manner, the conductance of ion channels can be made to be sensitive to chemical or environmental conditions, for example as isolated channels or as the output of a signaling pathway in an intact cell. As such, sensors can provide improved flexibility and sensitivity for chemical and environmental sensing platforms.

Figures 1A, 1B, 1C:
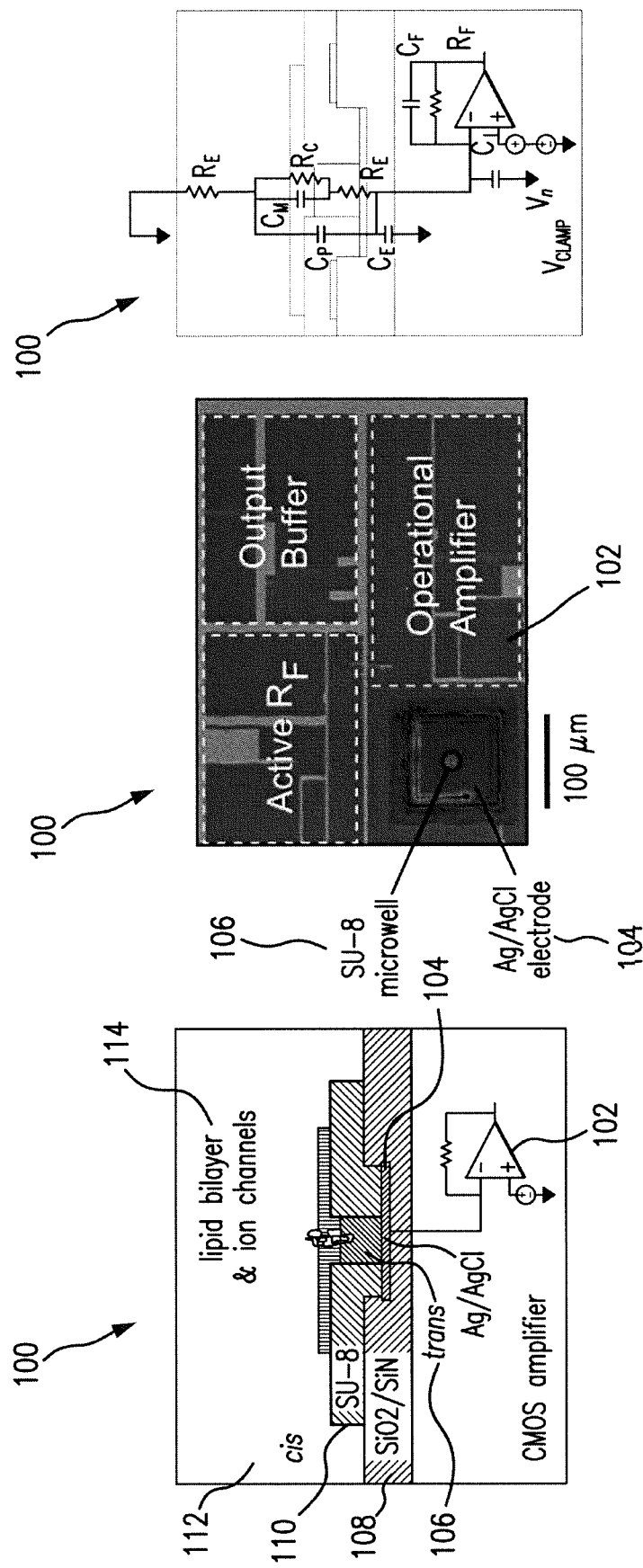
FIG. 1A is a diagram illustrating an exemplary biological ion channel interface according to the disclosed subject matter.
FIG. 1B is a diagram illustrating further features of the exemplary biological ion channel interface of FIG. 1A.
FIG. 1C is a circuit diagram illustrating further features of the exemplary biological ion channel interface of FIG. 1A.

FIG. 1A is a cross-sectional diagram illustrating an exemplary embodiment of a biological ion channel interface 100 according to the disclosed subject matter. A biological ion channel interface 100 includes an amplifier integrated circuit 102. Exemplary integrated circuits 102 for use with the biological ion channel interface 100 of the disclosed subject matter are shown and described in International Patent Application No. PCT/US12/026292, which is incorporated by reference herein in its entirety. As embodied herein, the integrated circuit 102 can be a multi-channel voltage-clamp current preamplifier. For purpose of illustration and not limitation, and as embodied herein, integrated circuit 102 can be produced in a commercial 130-nm CMOS process. Alternatively, integrated circuit 102 can be formed using other semiconductor processes, such as a bipolar transistor process. The integrated circuit 102 can have a plurality of channels, and each channel can have dimensions of less than a millimeter per side. As such, and as embodied herein, integrated circuit can have 8 channels, each channel approximately 0.4 mm×0.5 mm, with a total chip size of approximately 3 mm×3 mm. Furthermore, for purpose of illustration and not limitation, integrated circuit 102 can be configured as a resistive feedback voltage-clamp current preamplifier or a capacitative feedback voltage-clamp current preamplifier.

The integrated circuit 102 can be processed to form microelectrodes 104, which can be, for example and without limitation, Ag/AgCl microelectrodes. The integrated circuit can be mounted on larger carrier wafers, for example using poly-methylmethacrylate (PMMA) as an adhesive, and photolithography can be performed to pattern photoresist (e.g., S1818, Shipley) over at least a portion of the of the integrated circuit 102 die, which can exclude the portion of the integrated circuit 102 including the amplifier input electrodes. Aluminum metallization from the amplifier input electrodes can be removed chemically (e.g., using Transene Aluminum Etchant Type A for 5 minutes in a 50° C. bath, followed by deionized water rinse). 5 nm Ti and 250 nm Ag can be deposited, for example using e-beam evaporation. A lift-off technique, for example using Remover PG (from Microchem), can be utilized to remove the photoresist with the metal remaining patterned on the microelectrodes 104.

Microwells 106, for example and embodied herein as SU-8 microwells, can be formed over or proximate to the microelectrodes 104. A forming gas (e.g., H2+Ar) plasma can be applied to treat the area, and a negative photoresist 110, for example and embodied herein as epoxy-based 5-μm-thick SU-8 2005 (from Microchem) can be spun on. The negative photoresist 110 can be patterned using UV photolithography to form wells, for example and embodied herein having a cross dimension of 20-μm to 30-μm, and can be aligned with and disposed proximate to the microelectrodes 104. FIG. 1B is a diagram illustrating an amplifier integrated circuit 102 processed with a thin-film silver microelectrode 104 and a SU-8 microwell 106.

The integrated circuit 102 can be wirebonded, for example and as embodied herein to a 272-pin ball grid array (BGA) package. The wirebonds can be covered with doughnut epoxy encapsulation (e.g., GE-116 dam, H70E fill, Epoxy Technology), leaving an inner portion of the integrated circuit 102 exposed. A removable fluid chamber 112, for example and as embodied herein having a volume of 1 mL, can be formed above the integrated circuit 102, for example by attaching a section of a polypropylene centrifuge tube to the surface of the BGA package using an adhesive, such as KWIK-CAST silicone adhesive (from World Precision Instruments). The adhesive can also be applied over at least a portion of the rest of the surface of the integrated circuit 102, for example about three-quarters of the surface, and thus exposing only one channel to the solution at a time.

The integrated circuit 112 can be mounted in a socket on a suitable circuit board, which can include power management circuits, analog biasing circuits, channel multiplexing logic and analog signal filters to facilitate operation of and interaction with the integrated circuit 112. The circuit board can include a power source, including one or more of a battery power source and a connection to a wall power outlet. In some embodiments, the circuit board can include signal filters, such as a differential 4th-order Bessel 1 MHz antialiasing filter, analog-to-digital converters, digital isolators, an input/output interface, such as a module (e.g., XEM3010, from Opal Kelly) containing a high-speed USB 2.0 interface, and a field programmable gate array.

The circuit board can be connected to a general computer processor, for example using a suitable interface, and received data can be processed using suitable signal data processing software, such as MATLAB (from Mathworks). Raw signal traces can be digitized, for example at 4 MS/s, and stored without further processing. Analysis can be preceded by digitally filtering traces to desired signal bandwidths, for example using finite impulse response low-pass filters in MATLAB or Igor Pro (from Wavemetrics).

The fluid chamber 112 can be filled with an electrolytic solution, for example and without limitation, and as embodied herein, potassium chloride. The microelectrode 104 can be chlorinated, for example by applying a chlorine solution, such as sodium hypochlorite. Additionally or alternatively, the microelectrode 104 can be chlorinated by applying a current through the microelectrode 104. A lipid membrane can be applied proximate the microwell 106. For example and without limitation, the lipid membrane can be a lipid solution, for example and as embodied herein a 0.5 μL DPhPC solution (10 mg/mL diphytanoyl phosphatidylcholine in n-decane), and can be applied using an air bubble at the tip of micropipette. The lipids can form bilayers 114 spanning the surface of the microwell 106, as illustrated in FIG. 1A. Alternatively, the lipid membrane can be a cellular membrane of a live cell, which can be applied proximate the microwell 106, for example by applying a pressure gradient between the live cell and the microwell 106, as discussed further herein.

The lipid membrane covers the microwell 106 to electrically isolate the microwell 106. Multiple microwell 106 can be addressed in parallel, with independent trans Ag/AgCl microelectrodes 104 and one shared cis reservoir 112. The small volume of the covered microwell 106 (for example and without limitation of about 0.1 pL to 100 pL, and embodied herein as about 1.6 picoliters), also referred to as a trans chamber, can extend the life of the Ag/AgCl microelectrodes 104. However, the trans chamber can be inaccessible for solution perfusion after the bilayer 114 is formed.

Ag/AgCl microelectrodes 104 can deplete over time, and the mass of available silver can determine the total charge ($Q=I_{DC} \times t$) that can be measured over the lifetime of the sensor. Lower DC currents can be utilized for ion channels as compared to solid-state nanopores, and thus a thin evaporated silver film layer can be utilized for the microelectrode 104 rather than a thicker electroplated layer. The microelectrode 104, embodied herein having dimensions of 100 μm×100 μm×250 nm, can include approximately 21 ng of silver, which, when converted to AgCl, can corresponds to a charge transfer of 19 μC. As such, each microelectrode 104 can have a lifetime of about 2 days at 100 pA bias. The small volume of the trans chamber can help to resist dissolution of the AgCl. Although AgCl can have a solubility in water of $K_{SP}=1.8 \times 10^{-10}$, 2 pL of water can become saturated with AgCl after dissolving 50 femtograms of AgCl. As such, each microelectrode can have a lifetime of at least several hours.

FIG. 1C illustrates a representative equivalent circuit model for the expected measurement capacitances of the interface 100 overlaid onto the diagram of FIG. 1A. A DPhPC bilayer with a nominal diameter of 20 μm can have a capacitance $C_M=1.4$ pF. Other capacitances, such as between the 100 μm electrode and the Si substrate 108 ($C_E$), and between the covered portion of the electrode 104 and the electrolytic solution ($C_P$), can contribute a capacitance of about 120 fF. The capacitance of the amplifier 102 ($C_I$) can be 1 pF, and the feedback capacitance ($C_F$) can 0.15 pF. As such, the total capacitance can add up to an expected total of $\Sigma C \infty 3$ pF.

Figure 2:
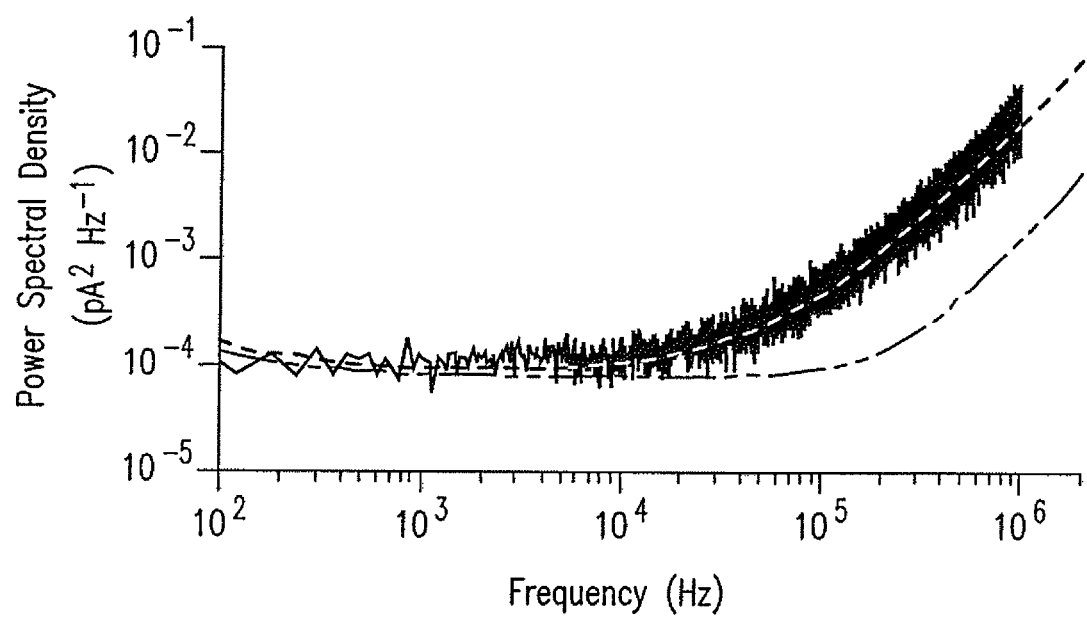
FIG. 2 is a diagram illustrating further features of the exemplary biological ion channel interface of FIG. 1A.

FIG. 2 illustrates measured input-referred noise power spectral density ($A^2$ $Hz^{-1}$) for a dry open-headstage condition (i.e., with no input) and with a DPhPC lipid bilayer 114 formed over a 20-μm-diameter microwell. Below 10 kHz, the noise can be determined by the amplifier 102 feedback network. At higher frequencies, the presence of the electrolyte in the microwell 106 and the bilayer 114 can increase the noise density as a function of $\Sigma C=(C_I+C_F+C_M+C_E+C_P)$. A fourth-order low-pass Bessel filter can be applied at various cutoff frequencies ($f_c$), and thus the noise baseline in the presence of the bilayer 114 can correspond to 1 $pA_{RMS}$ for $f_c=10$ kHz, 4.4 $pA_{RMS}$ at 100 kHz, 11.8 $pA_{RMS}$ at 250 kHz, and 61 $pA_{RMS}$ at 1 MHz.

The low-frequency noise density of the amplifier integrated circuit 102 (~10 fA $Hz^{-1/2}$) can be comparable to the thermal noise of a 150 MΩ resistor, which can be suitable for recordings of phenomena at noise amplitudes below 1 $pA_{RMS}$, and can be more suitable using discrete GΩ transimpedance stages. As such, low-frequency noise reductions can be challenging, while, high-frequency noise can be naturally reduced. In this manner, miniaturization can decrease capacitive parasitics, and for many ion channels, which can pass tens of picoamperes or more, an integrated platform can provide finer temporal resolution.

Example 1

The CMOS-anchored lipid bilayer membrane 114 can be tested by performing measurements of gramicidin, an antibiotic peptide which can increase the permeability of cell membranes. Gramicidin can produce transient dimer channels in lipid bilayers and form a junction between peptides in opposing halves of the membrane. Gramicidin ion channels can form and dissociate after some period of time, irrespective of voltage, yielding stepwise current changes in voltage-clamp recordings.

Figure 3:
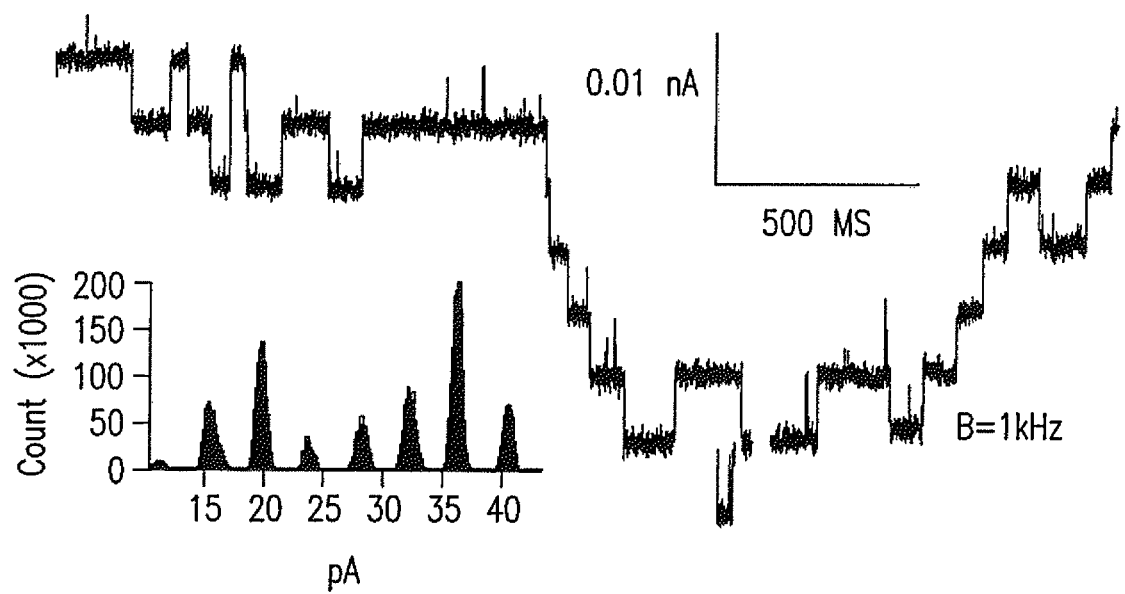
FIG. 3 is a diagram illustrating further features of the exemplary biological ion channel interface of FIG. 1A.

Gramicidin recordings were demonstrated using the interface 100. Prior to forming a bilayer, up to 0.5 μL gramicidin solution (1 μg/mL in ethanol) was added to the electrolytic solution, and as such the gramicidin solution was present in both the cis and trans chambers. After applying the lipid bilayer 114, random stepwise current fluctuations were observed. FIG. 3 illustrates recordings of single gramicidin channels in the amplifier-attached lipid bilayers 114. The trace was measured in 1M KCl at 100 mV bias, and digitally filtered to 1 kHz bandwidth. The inset shows a histogram illustrating the current levels in the presented trace. FIG. 3 shows multiple simultaneously active channels producing discrete current levels separated by approximately 4 pA.

Example 2

For an exemplary biotechnology applications of the interface 100, alpha hemolysin (α-HL), a bacterial toxin that can form heptameric ion channels in cell membranes, was recorded. α-can be utilized as a nanopore sensor, with potential for high-speed DNA sequencing, among other applications. The channel of an α-HL pore can have a diameter of approximately 1.4 nm at its smallest constriction, and the presence of small molecules within a single channel can measurably modulate its ionic conductance.

FIG. 4A illustrates measurements of a single alpha-hemolysin channel in the presence of polydisperse polyethylene glycol (PEG, average m.w. 1500). Each rectangular current blockade corresponded to a single PEG molecule occupying the channel. The trace is shown at B=100 kHz. FIG. 4B shows an all-points histogram of the trace of FIG. 4A, illustrating separation between open and blocked current levels. FIG. 4C is an enlarged view of a representative PEG event, at 50 kHz and 250 kHz bandwidths. FIG. 4D is an enlarged view of a the falling edge of a representative PEG event, contrasting the edge rates at 10 kHz, 50 kHz, and 250 kHz bandwidth. FIG. 4E is a histogram illustrating the average residual current in 7,642 events with durations of at least 0.5 ms. Each peak in the histogram corresponds to a unique PEG polymer length.

As shown in FIGS. 4A-4D, at +50 mV bias, the steady-state current through the pore was measured to be 200 pA, and intermittent blockage events decreased this current to approximately 25% of its open value. Each of these blockages corresponded to a single PEG molecule temporarily occupying the pore. The residual current during each of these events was suitably stable, and at a signal bandwidth of 250 kHz, the event edges appeared suitably sharp.

A range of PEG polymer lengths were present in the solution, and each size molecule can modulate the α-HL conductance by a different degree. Producing a histogram of the average residual current level during each event can yield a histogram with discrete levels corresponding to the distinct PEG polymer lengths. FIG. 4E shows a histogram of the average depths of 7,642 events recorded over 6 minutes. The histogram shows distinct peaks separated by approximately 2 pA and each having a standard deviation of about 0.5 pA. The appearance of discrete peaks illustrates the stability of the amplifier integrated circuit 102, electrodes 104, bilayer 114, and α-HL channel over the length of this trace. Each point in the histogram can represent the average of all points in an event, and as such each point can have an expected error roughly corresponding to the integrated noise density from DC to ½τ, where can represent the duration of the events. By including all events longer than 0.5 ms, the peaks can have a standard deviation represented as $$10 \frac{fA}{\sqrt{Hz}} \times \sqrt{\frac{1}{2 \times 0.5 \text{ ms}}} \approx 0.5 \text{ pA}.$$

As such, the deviation can be higher than typical deviations of discrete amplifiers, yet the interface 100 provides extended dynamic range and smaller physical size.

Example 3

Another example of a reconstituted ion channel is alamethicin, which can present a relatively large conductance and thus can tolerate the noise levels which can accompany higher bandwidths. Alamethicin is a 20-amino-acid peptide that can assemble into small homomeric clusters in lipid bilayers. These peptide groups can form voltage-gated ion channels with discrete conductance levels that can correspond to integer numbers of alamethicin molecules. The conductance levels can have a quadratic dependence on the level number, and can appear as characteristic staircase current patterns in voltage-clamp recordings.

After forming lipid bilayers 114 proximate the amplifier integrated circuit 102, 1 μL of 10 μg/mL alamethicin in ethanol was added to the cis chamber 112. FIG. 5A illustrates recordings of single alamethicin channel bursts in 4M KCl at 150 mV bias, digitally filtered to 50 kHz bandwidth. As shown in FIG. 5A, channel current bursts appeared at negative bias voltages. FIG. 5B is an all-points histogram of the trace of FIG. 5A, showing three distinct conductance levels. FIG. 5C shows the discrete current levels identified in the histogram, illustrating a quadratic dependence on the level number. FIG. 5D is an enlarged view of a representative channel burst, identified by arrow 5D in FIG. 5A.

Alamethicin gating transitions can occur faster than can be resolved by certain patch-clamp amplifiers. The higher signal bandwidth of interface 100 can be suitable to examine these conductance transitions. FIG. 6A is an enlarged view of the rising edge of the alamethicin channel burst shown in FIG. 5D, sampled at 4 MS/s and digitally filtered to 50 kHz and 1 MHz bandwidths, At 1 MHz, FIG. 6A shows that transition between L1 and L3 includes two brief stays at L2, with the second one lasting only 3 μs. FIG. 6B is an enlarged view of the falling edge of the channel burst of FIG. 5D. As shown in FIG. 6B, the transitions can be considered sharp, even at 1 MHz. As such, these transitions can occur in less than 500 ns.

FIGS. 7A-7D each illustrates an alternative embodiment of an interface formed with lipid bilayers according to the disclosed subject matter. As shown in FIGS. 7A-7B, interface 200 can include a separately fabricated bilayer support 210 having one or more nanoscale apertures 206 placed into an electrolytic solution 212 aligned with and proximate to integrated circuit 202. The bilayer support can be a hydrophobic support (as shown in FIG. 7A) or a hydrophobic support (as shown in FIG. 7B). Ag/AgCl electrodes 204 can be formed on the integrated circuit 202 as described herein. Lipids in oil, such as n-octane, n-decane, n-hexadecane or any other suitable lipids, can be applied in a thin layer over the aperture 204 to faun a lipid bilayer 214 at the aperture 204. Alternatively, the bilayer support 210 can be exposed to unilamellar lipid vesicles, which can fuse to the bilayer support 210 proximate the one or more apertures 206 to form the lipid bilayer 214. A gasket 208 can be used separate multiple channels, for example as shown in FIG. 7B. An external electrode 216 can be placed in the electrolytic solution 212 on the opposite side of the bilayer support 210.

FIG. 7C illustrates an alternative embodiment of an interface 300 having a tethered bilayers configuration. Interface 300 can include solid-supported lipid bilayers suitable metal) electrodes 304 on the surface of the integrated circuit 302. For example, the metal electrodes 304 can be initially covered by a self-assembled monolayer (SAM, 314 formed on metal (for example and without limitation, gold, platinum, or any other for example, 3-mercaptopropyl silane) 310, followed by lipid vesicle fusion to form a lipid bilayer 314 over the monolayer 310. Alternatively, the metal electrodes 304 can exposed to lipid vesicles containing chemical anchoring groups that adhere to the metal. An external electrode 316 can be placed in the electrolytic solution 312 on the opposite side of the lipid bilayer 314.

FIG. 7D illustrates an alternative embodiment of an interface 400 having multiple, lipid-sealed microwells. Interface 400 can include microwells 406 formed on the surface of an integrated circuit 402, as described herein with respect to interface 100, and microwells 406 can be separated by a gasket 408. Metal electrodes 404 can be formed on integrated circuit 402 as described herein. Lipids in oil and/or unilamellar lipid vesicles can be applied to form the lipid bilayer 414. An external electrode 416 can be placed in the electrolytic solution 412 on the opposite side of the lipid bilayer 414.

FIG. 7E illustrates an alternative embodiment of an interface 500 having a thru-chip configuration. Interface 500 can include one or more apertures 506 etched through integrated circuit 502. Lipids can be applied proximate the one or more apertures 506 to form one or more lipid bilayers 514 between front and back sides of the integrated circuit 502. A gasket 508 can be applied on one side of the integrated circuit to isolate multiple channels. An external electrode 516 can be placed in the electrolytic solution 512 on the opposite side of the integrated circuit 502.

While recordings of membrane proteins in reconstituted lipid bilayers can be useful for biophysical studies, certain applications can benefit from in situ observations of ion channels in intact cells. Such observations can be useful, for example, for measuring complex proteins and signaling pathways which are not easily recreated in a simplified planar bilayer. Working with intact cells can also be more convenient, as it can eliminate procedures to first isolate the desired proteins from cells, create a lipid bilayer, and induce the channels to insert into the lipid bilayer.

FIGS. 8A-8E each illustrates an alternative embodiment of an interface formed with giant unilamellar vesicles (GUVs) according to the disclosed subject matter. FIG. 8A illustrates an interface 600 having a separate planar patch aperture configuration. Interface 600 can include a separate "planar patch" substrate 610, embodied herein as a glass chip, having a nanoscale aperture 606 etched therethrough, and disposed in an electrolytic solution 612 aligned with and proximate to the integrated circuit 602. A pressure differential can be used to position and seal a cell 614 proximate the aperture. A gasket can be used between the substrate 610 and integrated circuit 602 to isolate multiple channels. Metal electrodes 604 can be formed on integrated circuit 602 as described herein. An external electrode 616 can be placed in the electrolytic solution 612 on the opposite side of the substrate 610.

FIGS. 8B-8C illustrate an interface 700 having a blind microwell configuration. Interface 700 can include small microwells 706 (for example and without limitation about 0.1 pL to 100 pL, and embodied herein as about 1.6 picoliters) fabricated on the surface of the integrated circuit 702, and cells 714 can aligned with and disposed proximate the microwells 706 through one or more of surface adhesion proteins, pressure and microfluidics. A gasket 708 can be used between the microwells 704 to isolate multiple channels. Metal electrodes 704 can be formed on integrated circuit 702 as described herein. An external electrode 716 can be placed in the electrolytic solution 712 on the opposite side of the substrate 710. Interface 700 can produce relatively dense arrays and can be suitable for looser "cell-attached" patch recordings. Additionally or alternatively, as shown in FIG. 8C, interface 700 can include one or more fluid or air microchannels 718 formed to access the microwells 706 on the surface of the integrated circuit 702. The buried microchannels 718 can be used to maintain a pressure differential across a cell, which can be utilized for "gigaohm-seal" formation with a cell 714. Buried microchannels 718 can also allow solution exchange on both sides of the cell 714.

FIG. 8D illustrates an exemplary interface 800 having a thru-chip configuration. Interface 800 can include an integrated circuit 802 having apertures etched directly through the integrated circuit 802 to form planar patch clamp apertures 806. This arrangement can allow simple access to both fluid reservoirs, for maintaining a pressure differential or exchanging fluid. Cells 814 can be applied on either side of the integrated circuit 802. A gasket 808 can be used to form microwells 806 and isolate multiple channels. Metal electrodes 804 can be formed on integrated circuit 802 as described herein. An external electrode 816 can be placed in the electrolytic solution 812 on the opposite side of the integrated circuit 802 from metal electrodes 804.

FIG. 8E illustrates an exemplary interface 900 having an integrated circuit 902 incorporated inside a pipette 906, such as a glass patch pipette. The pipette 906 can contain an electrolytic solution 908, and the integrated circuit 902, including one or more metal electrodes 904, can be at least partially disposed within the pipette 906. A cell 914 can be coupled to an end of the pipette 906 opposite the integrated circuit 902. A lead wire 910 can be coupled to the integrated circuit 902, for example at a portion of the integrated circuit 902 external to the pipette 906. Interface 900 can provide the flexibility and performance of a patch pipette, while reducing the size and parasitic capacitance of the associated headstage.

While the disclosed subject matter is described herein in terms of certain exemplary embodiments, those skilled in the art will recognize that various modifications and improvements can be made to the disclosed subject matter without departing from the scope thereof.

The foregoing merely illustrates the principles of the disclosed subject matter. Various modifications and alterations to the described embodiments will be apparent to those skilled in the art in view of the teachings herein. It will be appreciated that those skilled in the art will be able to devise numerous modifications which, although not explicitly described herein, embody its principles and are thus within its spirit and scope.

The invention claimed is:

1. A method for interfacing an integrated circuit with a biological ion channel, the integrated circuit being at least partially disposed within a chamber containing an electrolytic solution and including an amplifier and one or more electrodes on a surface thereof, comprising:

forming one or more microwells over the one or more electrodes and the amplifier;

applying a lipid membrane over a bilayer support disposed above the one or more microwells, wherein the lipid membrane and the one or more microwells are disposed within the chamber and further wherein the bilayer support is configured to fuse to the lipid membrane;

placing a further electrode in the electrolytic solution proximate the lipid membrane on a side opposite the integrated circuit, wherein the integrated circuit is formed using a semiconductor process; and inserting at least one portion of the integrated circuit into a first end of a pipette containing the electrolytic solution, wherein the at least one portion of the integrated circuit includes the amplifier and the one or more electrodes.

2. The method of claim 1, wherein the lipid membrane comprises a reconstituted lipid bilayer.

3. The method of claim 2, wherein the lipid bilayer comprises one or more reconstituted lipids in oil.

4. The method of claim 3, wherein the one or more reconstituted lipids comprise diphytanoyl phosphatidylcholine.

5. The method of claim 3, wherein the oil comprises n-octane, n-decane or n-hexadecane.

6. The method of claim 1, wherein the lipid membrane comprises a cellular membrane of a live cell.

7. The method of claim 6, wherein applying the lipid membrane comprises applying a pressure differential between the live cell and the one or more microwells.

8. The method of claim 7, further comprising forming microchannels along the integrated circuit proximate the one or more microwells to control the pressure differential proximate the one or more microwells.

9. The method of claim 1, wherein the one or more electrodes comprise an Ag/AgCl electrode.

10. A biological ion channel interface comprising:
an integrated circuit adapted to be at least partially disposed within a chamber containing an electrolytic solution and comprising an amplifier and one or more electrodes on a surface thereof;
an intermediate structure having one or more microwells formed therein and adapted to be disposed in the electrolytic solution over the one or more electrodes and the amplifier;
a lipid membrane disposed over a bilayer support disposed above the one or more microwells, wherein the lipid membrane and the one or more microwells are disposed within the chamber and further wherein the bilayer support is configured to fuse to the lipid membrane;
a further electrode adapted to be disposed in the electrolytic solution proximate the lipid membrane on a side opposite the integrated circuit, wherein the integrated circuit is formed using a semiconductor process; and
a pipette containing the electrolytic solution, wherein at least one portion of the integrated circuit is disposed in a first end of the pipette, wherein the at least one portion of the integrated circuit includes the amplifier and the one or more electrodes.

11. The interface of claim 10, wherein the lipid membrane comprises a reconstituted lipid bilayer.

12. The interface of claim 11, wherein the lipid bilayer comprises one or more reconstituted lipids in oil.

13. The interface of claim 12, wherein the one or more reconstituted lipids comprise diphytanoyl phosphatidylcholine.

14. The interface of claim 12, wherein the one or more reconstituted lipids comprise one or more unilamellar lipid vesicles.

15. The interface of claim 12, wherein the oil comprises n-octane, n-decane or n-hexadecane.

16. The interface of claim 10, wherein the lipid membrane comprises a cellular membrane of a live cell.

17. The interface of claim 16, further comprising one or more microchannels disposed along the integrated circuit proximate the one or more microwells to control a pressure differential between the one or more microwells and the live cell.

18. The interface of claim 10, wherein the one or more electrodes comprise an Ag/AgCl electrode.

19. A method for interfacing an integrated circuit with a biological ion channel, the integrated circuit including one or more electrodes over an amplifier on a surface thereof, comprising:
inserting a portion of the integrated circuit into a first end of a pipette containing an electrolytic solution, wherein the portion of the integrated circuit includes the one or more electrodes and the amplifier and further wherein the integrated circuit is formed using a semiconductor process;
coupling a cell to a second end of the pipette; and
placing an electrical lead wire on a remaining portion of the integrated circuit disposed outside of the pipette, wherein the pipette is configured as a patch pipette for living cells.

20. The method of claim 19, wherein the pipette comprises a glass patch pipette.

* * * * *